United States Patent [19]

Kaiser et al.

[11] 4,267,346
[45] May 12, 1981

[54] PROCESS FOR THE PREPARATION OF 1,2,4-TRIAZOLE

[75] Inventors: Reinhard Kaiser, Cologne; Guido Steffan, Odenthal, both of Fed. Rep. of Germany

[73] Assignee: Bayer Aktiengesellschaft, Leverkusen, Fed. Rep. of Germany

[21] Appl. No.: 612

[22] Filed: Jan. 2, 1979

[30] Foreign Application Priority Data

Jan. 20, 1978 [DE] Fed. Rep. of Germany ....... 2802491

[51] Int. Cl.$^3$ ............................................ C07D 249/08
[52] U.S. Cl. .................................................. 548/262
[58] Field of Search ..................... 260/308 R; 548/262

[56] References Cited

FOREIGN PATENT DOCUMENTS 61617 12/1970 Luxembourg ........................... 548/262

OTHER PUBLICATIONS

Ainsworth et al., J. Am. Chem. Soc., vol. 77, pp. 621–624 (1955).
Treybal, Mass Transfer Operations, (McGraw-Hill, 1955), pp. 8–9.

*Primary Examiner*—Alton D. Rollins
*Attorney, Agent, or Firm*—Sprung, Felfe, Horn, Lynch & Kramer

[57] ABSTRACT

A process for preparing 1,2,4-triazole which comprises contacting hydrazine with formamide in the molar ratio of 1:2.0–2.7 at a temperature from 100° to 250° C. in the presence of ammonia.

7 Claims, No Drawings

PROCESS FOR THE PREPARATION OF 1,2,4-TRIAZOLE

The invention relates to a process for the preparation of 1,2,4-triazole by reacting hydrazine with formamide.

It is known (Luxembourg 61,617) to prepare 1,2,4-triazole by reacting hydrazine with formamide in the temperature range from 90° to 260° C. using a molar ratio of 1 to 3.

A process has now been found for the preparation of 1,2,4-triazole by reacting hydrazine with formamide, which is characterised in that hydrazine is reacted with formamide in the molar ratio of 1:2.0 to 1:2.7 in the temperature range from 100° to 250° C. in the presence of ammonia.

The process according to the invention can be illustrated by the following equation:

$$H_2N-NH_2 + (3-n) H-C{\overset{O}{\underset{NH_2}{\diagup}}} + n\, NH_3 \longrightarrow$$

$$\underset{0.3 \leq n \leq 1}{\text{[1,2,4-triazole]}} + 2H_2O + 2NH_3 + (1-n)\, CO$$

Commercially available ammonia can be employed as the ammonia for the process according to the invention, and in general is passed into the reaction mixture in the gaseous state or as a solution in a mixture of the starting materials and/or the reaction products.

The process according to the invention is preferably carried out in the presence of the ammonia given off in the reaction, all or some of which is recycled into the reaction.

The concentration of the ammonia in the reaction can vary within wide limits. However, it is appropriate in each case to introduce ammonia in an amount such that the reaction mixture is virtually saturated with ammonia.

The hydrazine for the process according to the invention can be employed both in the anhydrous state and in the form of hydrazine hydrate. Hydrazine hydrate is preferably employed, and can be present in concentrated or in dilute aqueous solution. In general, an aqueous hydrazine solution with a content of 20 to 70% by weight, preferably of 60 to 70% by weight, of hydrazine is used.

The formamide for the process according to the invention can be employed in the commercially available purity.

In the process according to the invention, hydrazine, formamide and ammonia are employed in the molar ratio of 1:2.0:1 to 1:<2.7:>0.3 preferbly 1:2.4:0.9 to 1:2.6:0.4.

The process according to the invention is carried out in the temperature range from 100° to 250° C., preferably from 110° to 220° C.

The process according to the invention can be carried out under normal pressure or under increased or reduced pressure. In general, it is appropriate to carry out the process according to the invention under normal pressure; however, using a slightly reduced pressure has the advantage, especially in the last phase of the reaction, that steam and gaseous waste products are removed more easily.

It is, of course, also possible to carry out the process according to the invention in the presence of an inert gas, for example nitrogen.

The process according to the invention can be carried out either discontinuously or continuously.

In a preferred embodiment of the process according to the invention, the reaction is carried out continuously in a multi-stage reactor cascade. It is particularly preferable to use 3 and 4-stage reactor cascades.

The process according to the invention can be particularly advantageously carried out when hydrazine hydrate is continuously reacted with formamide in a first stage of the reactor cascade in the molar ratio of 1:2.4 to 1:2.7 at temperatures from 100° to 120° C., the reaction mixture is then reacted in a second stage at 180° to 200° C., the gaseous ammonia-containing reaction products thereby formed are cooled to 110° to 150° C. and the condensate obtained is recycled into the second stage, the entire reaction mixture obtained in the second stage is then reacted in a third stage at 210° to 230° C., the gaseous ammonia-containing reaction products thereby formed are cooled to 40° to 80° C. and the condensate is recycled into the first stage, and the reaction product of the third stage is continuously removed.

In this procedure, some or all of the gaseous reaction products, which essentially contain ammonia, are recycled into the particular reaction stage.

However, the process according to the invention can also be carried out by passing the ammonia-containing gaseous reaction product in the first reaction stage into the second reaction stage and recycling at least some of the ammonia given off from the second stage with the volatile reaction products into the second stage, together with the condensate, and recycling into the first stage all or some of the ammonia passed from the second reaction stage into the third stage, together with the reaction mixture, and given off from this third stage, together with the volatile reaction product.

In a further embodiment, all of the reaction mixture formed in the first and second stage is passed into a third stage. In the third stage, the volatile reaction products are cooled to temperatures from 60° to 120° C. and all or some of the condensate the ammonia given off is recycled into the first stage.

The process according to the invention for the preparation of 1,2,4-triazole can be particularly advantageously carried out by allowing the reaction to proceed in a four-stage reactor cascade, choosing the temperature in the first three cascade stages as in the case of the three-stage reactor cascade and increasing the temperature in the fourth stage to 195° to 240° C. In this case, the volatile reaction products formed in the second stage are appropriately cooled to 110° to 140° C. and the condensate obtained is recycled into the second stage. The volatile reaction products obtained in the third and fourth stage are cooled together to 40° to 80° C. and the condensate is recycled into the first stage. After the fourth stage, the end product is continuously removed and isolated. It is also possible, of course, for the volatile reaction products given off from the third and fourth reaction stage to be cooled separately and for the condensates to be recycled separately or together.

The individual process variants can be carried out with various average residence times in the individual reaction stages of the reactor cascade. By average residence time there is understood the quotient of the capacity of the reactor and the sum of the volumes of the starting materials, at 20° C., which are introduced per hour into the first reactor.

The residence time in the first reactor stage is in general 5 to 150 minutes, preferably 20 to 40 minutes. The residence times in the subsequent reactor stages are about 20 to 200 minutes, preferably 40 to 120 minutes.

The reaction mixture obtained after the last stage is allowed to cool, and 1,2,4-triazole is obtained in high yields and can be employed in further reactions without additional purification.

1,2,4-Triazole is an intermediate product for the synthesis of dyestuffs, optical brighteners, anti-ageing agents, pharmaceutical formulations and agents for combating pests (Belgian Pat. No. 715,569, Belgian Pat. No. 729,878 and U.S. Pat. No. 3,293,259).

EXAMPLE 1

655 g/hour of formamide and 280 g/hour of hydrazine hydrate are simultaneously metered continuously into a 1 l multi-necked flask at 110°–115° C. Water and ammonia are given off as reaction products which are gaseous under the reaction conditions.

The reaction mixture present in the 1st reaction flask in the liquid state under the reaction conditions runs continuously over an overflow into a 2 l multi-necked flask, which is heated to about 190° C. The gaseous products given off are cooled to about 140° C. and the condensate thereby obtained is recycled into the 2nd reaction vessel.

The reaction mixture present in the 2nd flask in the liquid state under the reaction conditions runs continuously into a 1.5 l multi-necked flask, which is kept at about 215°–220° C. The gaseous products given off are cooled to 50°–55° C. and the condensate thereby obtained is recycled into the 1st flask.

The reaction mixture, present in the liquid state under the reaction conditions, leaving the 3rd reaction flask is cooled and thereby solidifies.

Yield: 382 g/hour of 95% pure 1,2,4-triazole, 94% of theory, relative to hydrazine hydrate.

Melting point: 112°–116° C.

EXAMPLE 2

The procedure followed is as in Example 1, but the reaction mixture present in the 3rd reaction flask in the liquid state under the reaction conditions runs continuously into a 1.5 l multi-necked flask, which is kept at 215°–220° C. The gaseous products given off are cooled to 50°–55° C. and recycled into the 1st flask. The 1,2,4-triazole is then isolated as described in Example 1.

Yield: 367 g/hour of 97.8% pure 1,2,4-triazole, 93% of theory, relative to hydrazine hydrate.

Melting point: 114°–116° C.

EXAMPLE 3

486 g/hour of formamide and 270 g/hour of hydrazine hydrate are simultaneously metered continuously into a 1 l multi-necked flask at 110°–115° C. The reaction mixture present in the 1st reaction vessel in the liquid state under the reaction conditions runs continuously over an overflow into a 2 l multi-necked flask, which is kept at 160° C. The gaseous reaction products formed under the reaction conditions in the 1st reactor are passed several times through the reaction mixture present in reactor 2. The reaction mixture of reactor 2 runs over continuously into a 1 l multi-necked flask, which is kept at 160° C. The gaseous products leaving reactor 2 are passed several times through the reaction mixture present in reactor 3.

The gaseous products leaving reactor 3 are cooled to 50°–80° C. The condensate is recycled into reactor 1.

The reaction mixture from reactor 3 runs over an overflow into a glass flask and is cooled there to 20°–30° C.

389 g/hour of 90% pure 1,2,4-triazole are obtained (=94% of theory, relative to hydrazine hydrate).

EXAMPLE 4

The reaction is carried out as in Example 3. However, in this case the gaseous reaction products given off from the 1st reactor are not passed through the reaction mixture present in the 2nd reactor but are passed several times, together with the gaseous reaction products given off from the 2nd reactor, through the liquid reaction mixture present in the 3rd reactor.

381 g of approximately 91% pure 1,2,4-triazole are obtained (=93% of theory, relative to hydrazine hydrate).

What is claimed is:

1. A process for preparing 1,2,4-triazole which comprises contacting hydrazne with formamide in the molar ratio of 1:2.0–2.7 at atmospheric pressure at a temperature from 100° to 250° C. in the presence of ammonia, all or part of the ammonia given off in the reaction being recycled into the reaction.

2. A process according to claim 1 wherein the reaction is carried out at a multi-stage reactor cascade.

3. A process according to claim 1 wherein the hydrazine is continuously reacted with formamide in a first stage of the reactor cascade at a temperature of 100° to 120° C., the reaction mixture is then reacted in a second stage of 180° to 200° C., the volatile reaction products thereby formed are cooled to 110° to 140° C. and the condensate obtained is recycled into the second stage, the entire reaction mixture obtained in the second stage is then reacted in a third stage at 210° to 230° C., the volatile reaction products thereby formed are to cooled to 40° to 80° C. and the condensate is recycled into the first stage and the end product is continuously removed from the third stage.

4. A process according to claim 1 wherein hydrazine, formamide and ammonia are employed in the molar ratio of 1:2.0:1 to 1:<2.7:>0.3.

5. A process according to claim 1 wherein the hydrazine, formamide and ammonia are employed in the molar ratio of 1:2.4:0.9 to 1:2.6:0.4.

6. A process according to claim 1 wherein the reaction mixture consists essentially of hydrazine, formamide and ammonia given off in the reaction.

7. A process according to claim 6 wherein the reaction mixture is saturated with ammonia.

* * * * *